(12) United States Patent
Shelton, IV

(10) Patent No.: US 7,451,904 B2
(45) Date of Patent: Nov. 18, 2008

(54) SURGICAL STAPLING INSTRUMENT HAVING END EFFECTOR GRIPPING SURFACES

(75) Inventor: Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 11/235,591

(22) Filed: Sep. 26, 2005

(65) Prior Publication Data

US 2007/0068989 A1 Mar. 29, 2007

(51) Int. Cl.
*A61B 17/072* (2006.01)

(52) U.S. Cl. .................. 227/181.1; 227/19; 227/179.1; 227/180.1; 227/178.1

(58) Field of Classification Search ............. 227/176.1, 227/19, 179.1, 180.1, 181.1, 182.1, 155; 606/219
See application file for complete search history.

(56) References Cited

U.S. PATENT DOCUMENTS

| | | | | |
|---|---|---|---|---|
| 4,429,695 A | * | 2/1984 | Green | 227/176.1 |
| 5,014,899 A | | 5/1991 | Presty et al. | |
| 5,071,430 A | * | 12/1991 | de Salis et al. | 606/219 |
| 5,307,976 A | * | 5/1994 | Olson et al. | 227/175.3 |
| 5,318,221 A | * | 6/1994 | Green et al. | 227/178.1 |
| 5,366,477 A | * | 11/1994 | LeMarie et al. | 606/208 |
| 5,397,324 A | * | 3/1995 | Carroll et al. | 606/139 |
| 5,423,471 A | * | 6/1995 | Mastri et al. | 227/181.1 |
| 5,452,837 A | | 9/1995 | Williamson, IV et al. | |
| 5,484,451 A | * | 1/1996 | Akopov et al. | 606/139 |
| 5,487,500 A | * | 1/1996 | Knodel et al. | 227/181.1 |
| 5,573,541 A | * | 11/1996 | Green et al. | 606/143 |
| 5,680,982 A | * | 10/1997 | Schulze et al. | 227/175.1 |
| 5,695,522 A | * | 12/1997 | LeMaire et al. | 606/208 |
| 5,697,542 A | * | 12/1997 | Knodel et al. | 227/175.1 |
| 5,833,695 A | * | 11/1998 | Yoon | 606/139 |
| 6,443,973 B1 | * | 9/2002 | Whitman | 606/219 |
| 6,755,338 B2 | * | 6/2004 | Hahnen et al. | 227/175.1 |
| 7,070,083 B2 | * | 7/2006 | Jankowski | 227/176.1 |
| 2002/0165541 A1 | * | 11/2002 | Whitman | 606/48 |
| 2003/0009193 A1 | * | 1/2003 | Corsaro | 606/207 |
| 2004/0232199 A1 | | 11/2004 | Shelton et al. | |
| 2006/0212069 A1 | * | 9/2006 | Shelton, IV | 606/205 |

FOREIGN PATENT DOCUMENTS

EP 1 090 592 4/2001

OTHER PUBLICATIONS

EPO Search Report, Appplication No. 06254953.0, Feb. 5, 2007, pp. 1-8.

* cited by examiner

*Primary Examiner*—Brian D Nash

(57) ABSTRACT

A surgical instrument for being endoscopically or laparoscopically inserted through a cannula of a trocar into an insufflated body cavity or lumen ("surgical site") for simultaneous stapling and severing of tissue including gripping surfaces on inner surfaces of an upper and lower jaw that enhance use as a grasping instrument to preposition tissue prior to performing a stapling and severing procedure. An illustrative version advantageously includes a separate closure trigger and closure mechanism that facilitates use as a grasper without the possibility for inadvertent firing (i.e., stapling and severing).

10 Claims, 5 Drawing Sheets

US 7,451,904 B2

SURGICAL STAPLING INSTRUMENT HAVING END EFFECTOR GRIPPING SURFACES

FIELD OF THE INVENTION

The present invention relates in general to surgical stapler instruments that are capable of applying lines of staples to tissue while cutting the tissue between those staple lines and, more particularly, to improvements relating to stapler instruments and improvements in processes for forming various components of such stapler instruments including adding bolstering material to the severed and stapled tissue.

BACKGROUND OF THE INVENTION

Endoscopic and laparoscopic surgical instruments are often preferred over traditional open surgical devices since a smaller incision tends to reduce the post-operative recovery time and complications. The use of laparoscopic and endoscopic surgical procedures have been relatively popular and has provided additional incentive to develop the procedures further. In laparoscopic procedures, surgery is performed in the interior of the abdomen through a small incision. Similarly, in endoscopic procedures, surgery is performed in any hollow viscus of the body through narrow endoscopic tubes inserted through small entrance wounds in the skin.

Laparoscopic and endoscopic procedures generally require that the surgical region be insufflated. Accordingly, any instrumentation inserted into the body must be sealed to ensure that gases do not enter or exit the body through the incision. Moreover, laparoscopic and endoscopic procedures often require the surgeon to act on organs, tissues and/or vessels far removed from the incision. Thus, instruments used in such procedures are typically long and narrow while being functionally controllable from a proximal end of the instrument.

Significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of translating wedges which, when driven distally, pass through openings in the staple cartridge and engage drivers supporting the staples to effect the firing of the staples toward the anvil.

Recently, an improved surgical stapling and severing instrument enhances clinical flexibility for both positioning tissue as well as stapling and severing, as described in U.S. pat. appln. Ser. No. 10/441,580, entitled "Surgical Stapling Instrument Having a Firing Lockout for an Unclosed Anvil", filed on Jun. 20, 2003, the disclosure of which is hereby incorporated by reference in its entirety. A separate closure trigger allows use as a grasper without the risk of inadvertent firing (i.e., simultaneous stapling and severing). While a successful approach, further enhancements would be desirable so that a surgical stapling and severing instrument may serve as a grasper.

Consequently, a significant need exists for an improved surgical stapling and severing instrument that incorporates a staple applying assembly (end effector) that effectively grips tissue for prepositioning prior to performing a stapling and severing procedure.

BRIEF SUMMARY OF THE INVENTION

The invention overcomes the above-noted and other deficiencies of the prior art by providing a surgical instrument that incorporates a surgical stapling instrument that has a lower jaw that upwardly dispenses staples that are formed against an inner surface of a pivotally attached upper jaw. A handle operates through an elongate shaft to to dispense and form the staples through clamped tissue. Prior to stapling, a trigger may be selectively employed to open and close the upper jaw while manipulating the handle, and thus the jaws, as a grasper to position tissue in preparation for stapling or other purposes. A nonplanar gripping surface on an inner surface of the jaws advantageously assists in gripping the tissue for positioning. Thereby, clinical flexibility and efficiency is enhanced.

In one aspect of the invention, gripping surfaces on both inner surfaces of the opposing jaws cooperate in grasping tissue.

In yet another aspect of the invention, a separate closure trigger and firing trigger enhance operation as a grasping instrument in conjunction with the gripping surfaces prior to actuating the firing trigger to operate as a stapling and severing instrument.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

Figure 1:
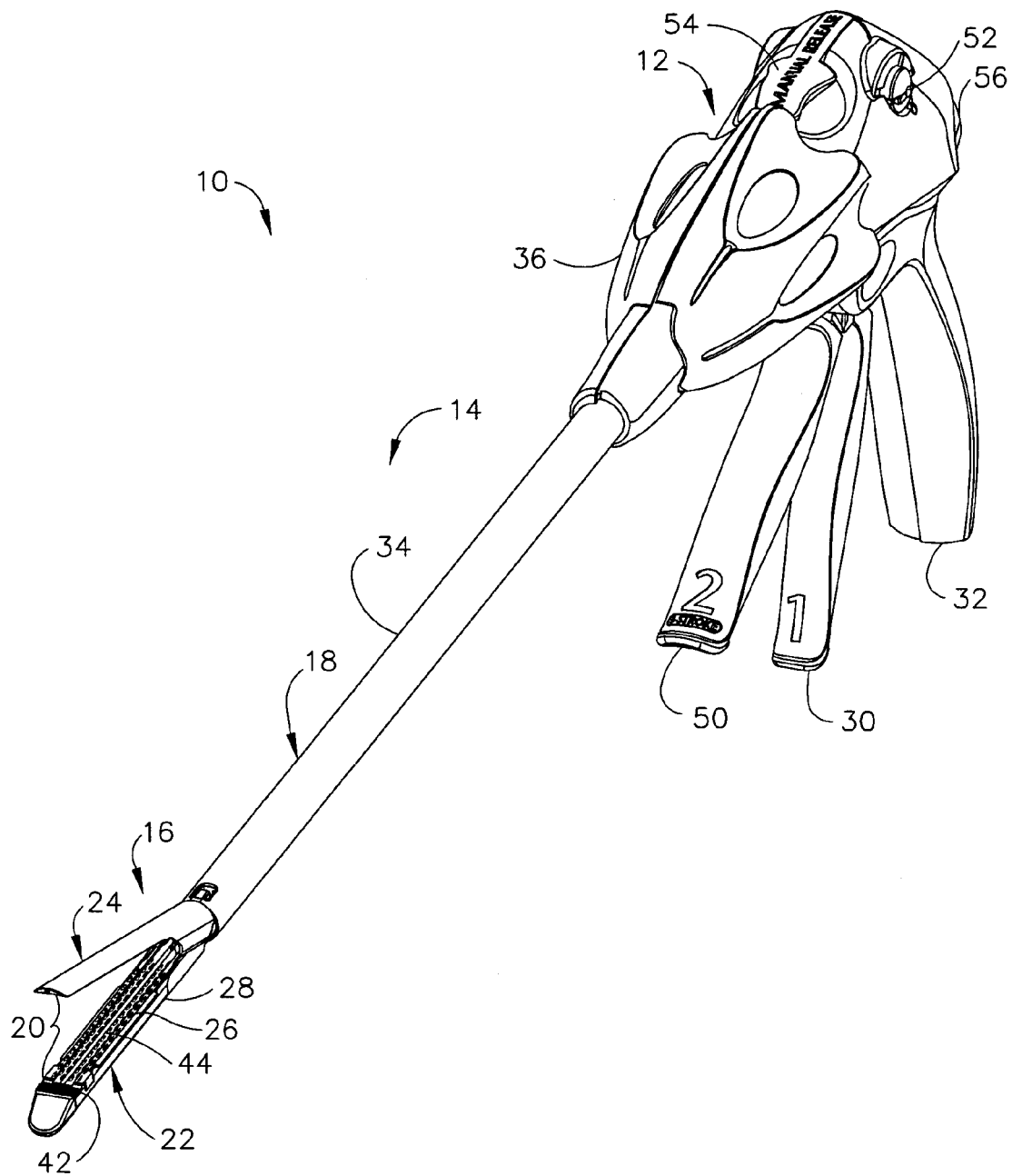
FIG. 1 is a left isometric view in elevation of a surgical stapling and severing instrument with an open end effector (staple applying assembly) having tissue gripping surfaces.
Figure 2:
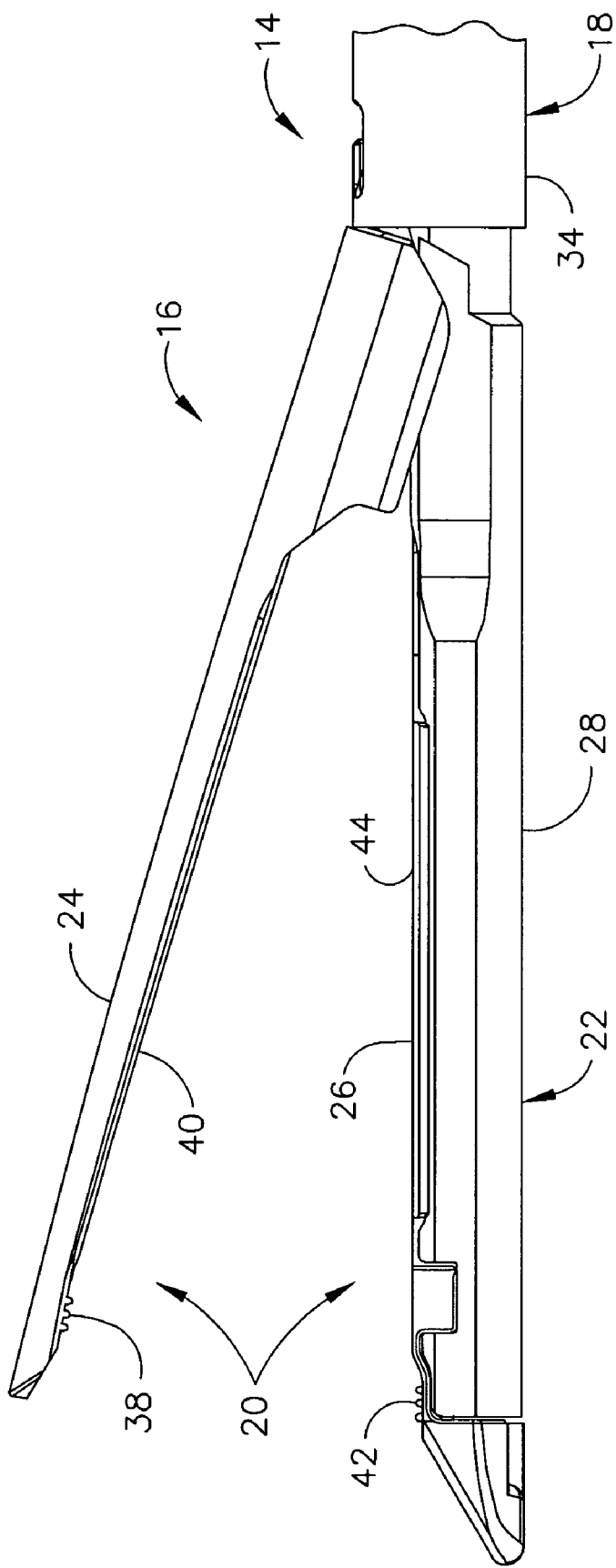
FIG. 2 is a left side view of the staple applying assembly of FIG. 1 with opposing gripping surfaces on each open jaw.
Figure 3:
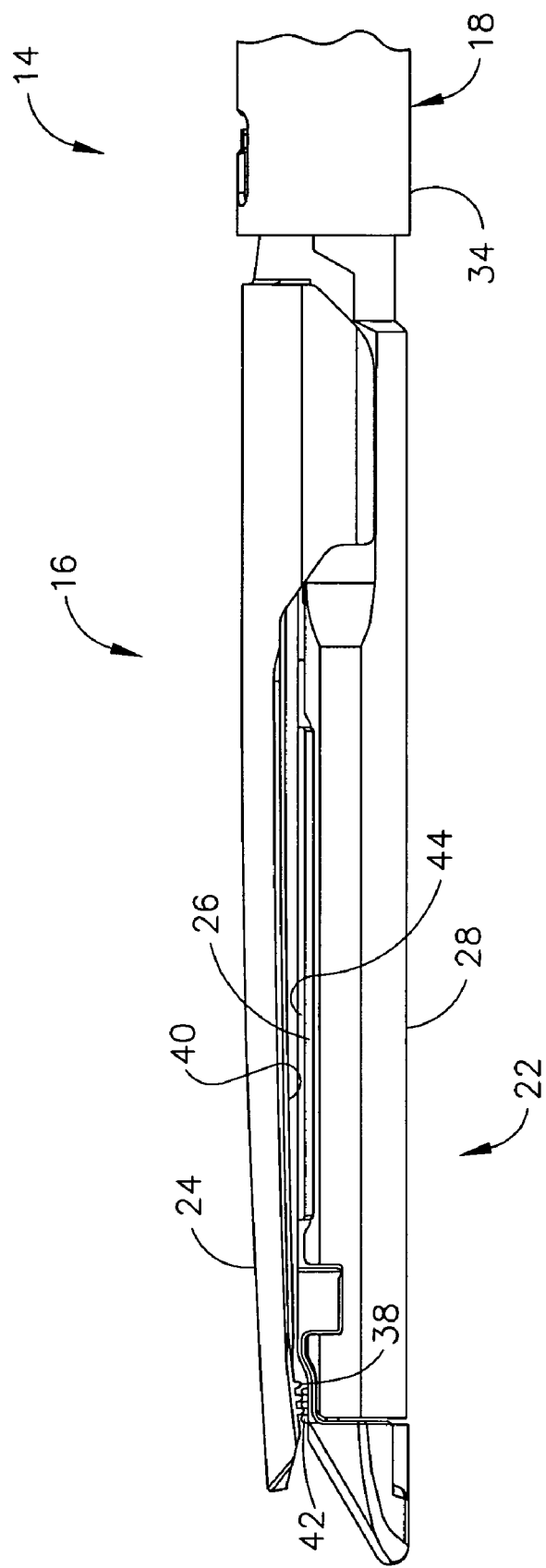
FIG. 3 is a left side view of the staple applying assembly of FIG. 2 with closed jaws and nonplanar, loosely enmeshing (interdigitating) gripping surfaces.
Figure 4:
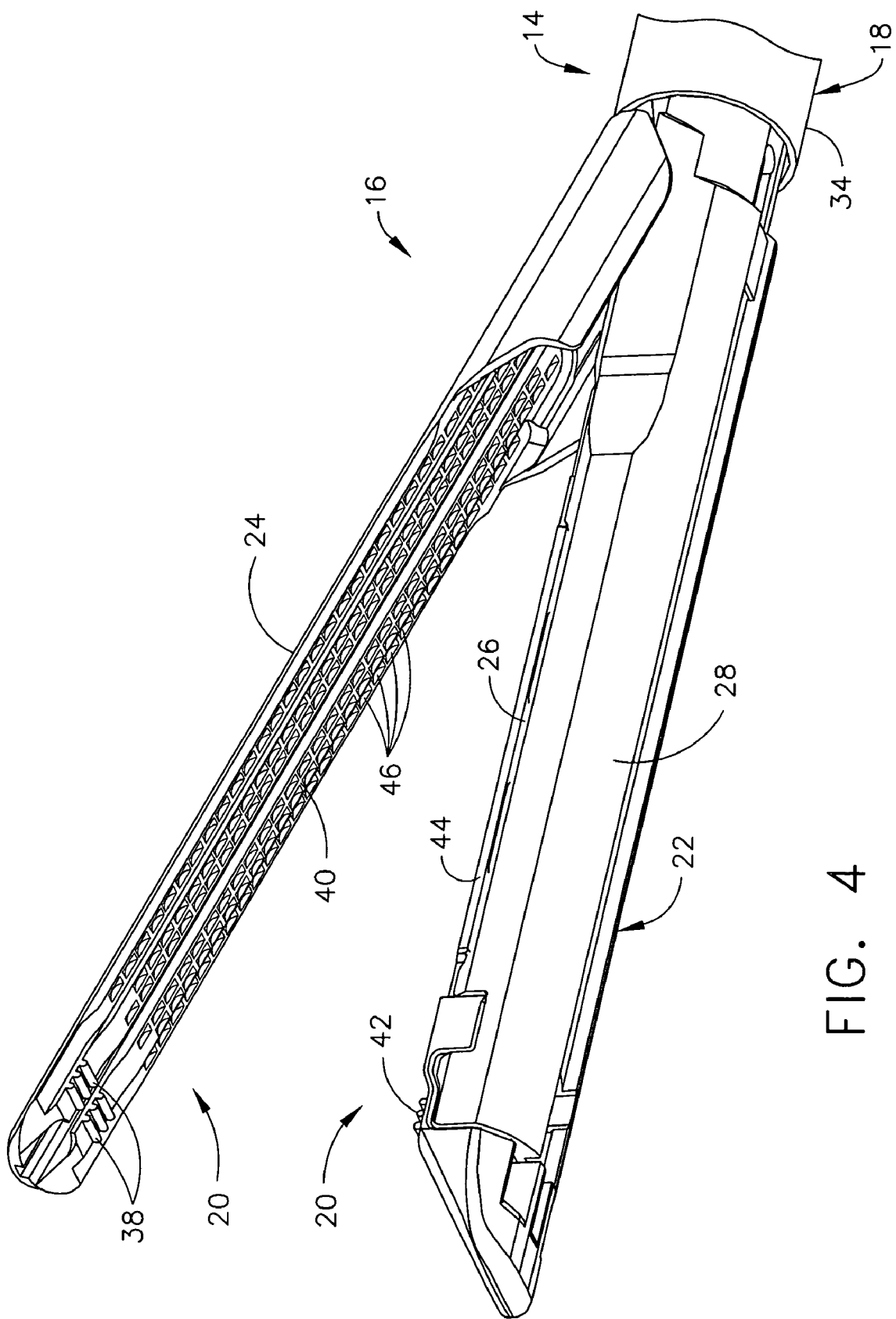
FIG. 4 is a lower left isometric view of the staple applying assembly of FIG. 2 with open jaws.
Figure 5:
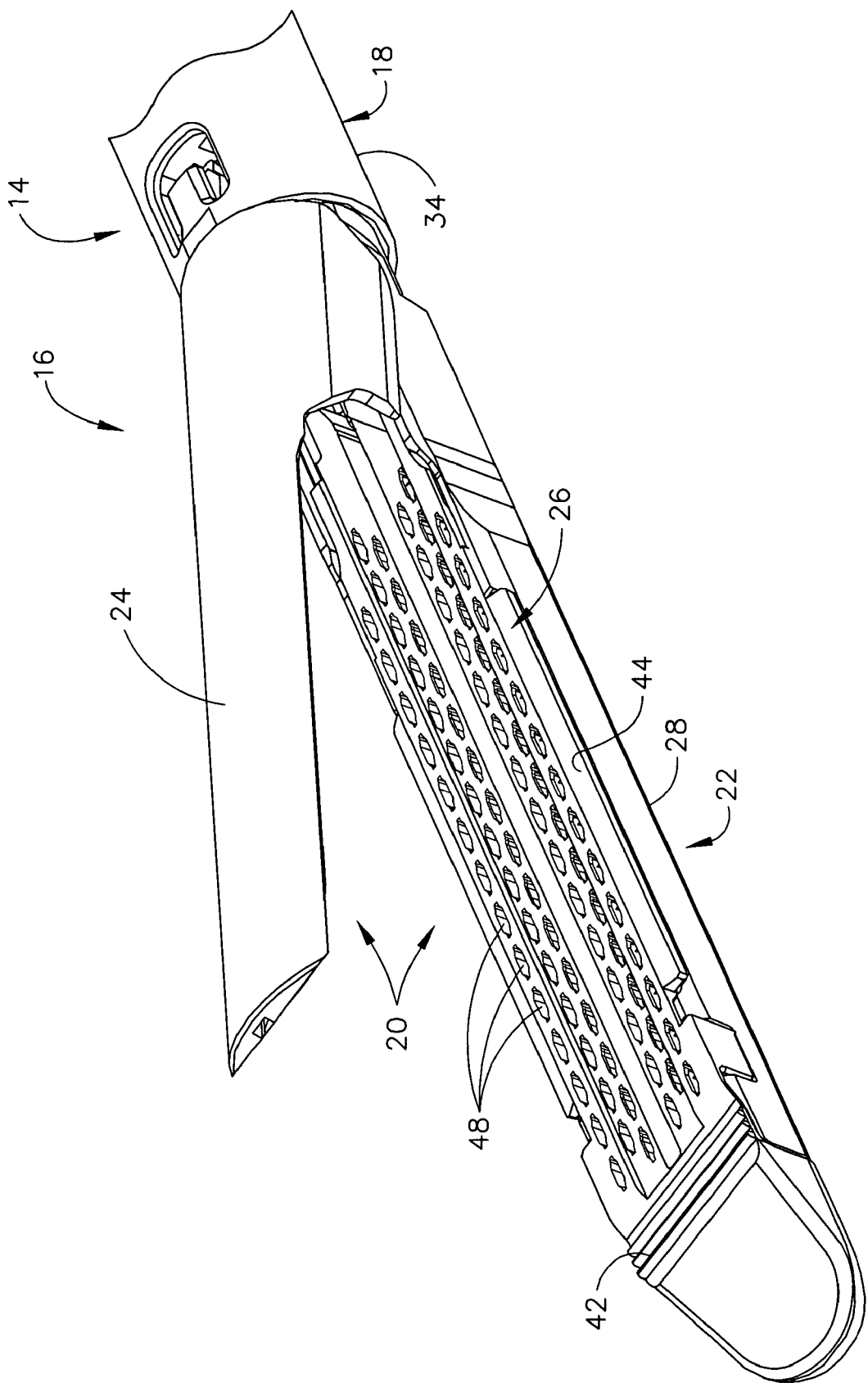
FIG. 5 is an upper left isometric view of the staple applying assembly of FIG. 2 with open jaws.

Turning to the Drawings, wherein like numerals denote like components throughout the several views, in FIGS. 1-5, a surgical stapling and severing instrument 10 includes a handle portion 12 (FIG. 1) that manipulates to position an implement portion 14 formed from a fastening end effector, specifically a staple applying assembly 16, distally attached to an elongate shaft 18. The implement portion 14 is sized for insertion through a cannula of a trocar (not shown) for an endoscopic or laparoscopic surgical procedure. With the exception of features described here to add gripping surfaces 20 to inner surfaces of a lower jaw 22 and a pivotally attached upper jaw (anvil) 24 that form the end effector 16, the surgical stapling and severing instrument 10 is as described in U.S. pat. appln. Ser. No. 11/052,387 entitled "Surgical Stapling Instrument Incorporating A Multi-Stroke Firing Mechanism With Return Spring Rotary Manual Retraction System" to Shelton et al., the disclosure of which is hereby incorporated by reference in its entirety. These gripping surfaces 20 enhance use as a grasper and enhance positioning of tissue during severing and stapling.

In use, a staple cartridge 26 is inserted into an elongate staple channel 28 to form the lower jaw 22 as depicted. A surgeon pivots a closure trigger 30 toward a pistol grip 32 of the handle portion 12. Thereby, a closure sleeve 34 is distally translated to pivot shut the anvil 24. The implement portion 14 may then be inserted into a cannula of a trocar in an insufflated body cavity or lumen. The surgeon may rotate the implement portion 14 about its longitudinal axis by twisting a shaft rotation knob 36 that engages across a distal end of the handle 12 and a proximal end of the elongate shaft 18.

Thereafter, the closure trigger 30 may be repeatedly manipulated and the handle 12 positioned in order to grasp and move tissue. Upper lateral gripping ridges 38 (FIGS. 2-4) proximate to a distal end on an inner surface 40 of the anvil 24 cooperate with lower lateral gripping ridges 42 (FIGS. 1-5) on an inner surface 44 of the lower jaw 22. When the jaws 22, 24 are closed, the upper and lower gripping ridges 38, 42 loosely enmesh to form a strong grip on interposed tissue to assist in positioning. Shaping of staple forming apertures 46 (FIG. 4) on the inner surface 40 of the anvil 24 and staple dispensing apertures 48 (FIG. 5) in the inner surface 44 of the staple cartridge 26 may advantageously enhance the grip on tissue more proximally placed in the staple applying assembly 16.

In FIG. 1, once satisfied with the positioning of the jaws 22, 24 on tissue, the surgeon further depresses the closure trigger 30 until the closure trigger 30 locks in position proximate to the pistol grip 32. Then a firing trigger 50 is depressed, perhaps multiple times, with firing progress indicated on a firing gauge 52 on the handle portion 12. The firing trigger 50 is drawn toward the closure trigger 24 and pistol grip 26 to distally advance a firing member (not shown) within the elongate shaft 18 to effect stapling and severing within the staple applying assembly 16. Then, the firing trigger 50 is released. If the firing member does not retract automatically, the surgeon raises a manual retraction lever 54 to assist in retraction. Then, a closure release button 56 is depressed to unlock the closure trigger 30 to open the staple applying assembly 16 and thereby release the stapled, severed ends of tissue.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

While lateral ridged surfaces 38, 42 are depicted, it should be appreciated that a toothed surface, a knurled surface, etc. may be used.

As a further example, although the illustrative version includes a gripping portion disposed distal to the stapling and severing region of the staple applying assembly 16, applications consistent with the present invention may include staple cartridges contoured to enmesh with mirror image contour of the inner surface of the anvil to increase the grip. For instance, outer lateral edges of each of the anvil and elongate channel may include loosely enmeshing rack segments along their length.

As an additional example, although the surgical stapling and severing instrument has a separate closure trigger and firing trigger, applications consistent with aspects of the invention may include those with a single trigger that sequentially closes the end effector and with further movement causes severing and stapling.

For another example, while a manually operated surgical stapling and severing instrument 10 is depicted for clarity, it should be appreciated that robotically manipulated and/or controlled fastening devices may incorporate a force controlled firing bar.

What is claimed is:

1. A surgical instrument, comprising:
an elongate shaft defining a longitudinal axis;
a lower jaw extending distally from the elongate shaft and operatively configured to upwardly dispense staples through a staple ejecting portion, the staple ejecting portion comprising at least one staple ejecting surface thereon which has a substantially flat portion and a central trench portion stepped downwardly from the substantially flat portion, wherein both the substantially flat portion and the central trench portion extend distally in the longitudinal direction to define the staple ejecting surface, wherein the staple ejecting portion further contains staples recessed below the staple electing surface, the lower jaw further comprising a step recessed into the lower jaw distal to the staple ejecting surface, the step having a step surface extending distally and parallel to the longitudinal axis, the step surface oriented with the substantially flat portion of the staple ejecting surface and stepped downwardly therefrom;
an upper jaw pivotally attached to the lower jaw and having a staple forming surface thereon which has a substantially flat clamping portion and a downwardly extending rib portion with both the substantially flat clamping portion and the rib portion extending distally in the longitudinal direction and containing staple forming pockets recessed therein, the staple forming surface positionable from an open position to a closed position proximate to the staple ejecting surface of the lower jaw, wherein when the staple forming surface is in the closed position, the downwardly extending rib portion is received within the trench portion of the staple ejecting surface;
a handle portion proximally attached to the elongate shaft and operatively configured to drive the staples from the lower jaw;
a trigger attached for movement to the handle portion operatively configured to close the upper jaw;
an upper gripping portion downwardly disposed on an angled surface of the upper jaw distal to and spaced away from the staple forming surface, the upper gripping portion oriented towards the step surface of the lower jaw; and
a lower gripping portion upwardly disposed on the step surface of the lower jaw, wherein the lower gripping portion is located distal to and spaced away from the staple ejecting surface, the step surface being parallel to the longitudinal axis and oriented with the staple ejecting surface and stepped therebelow, wherein the upwardly disposed lower gripping portion is recessed below the at least one staple ejecting surface;

wherein when said trigger is actuated to close the upper jaw proximate to the lower jaw, the upper gripping portion and the lower gripping portion intermesh below the staple ejecting surface at an angle.

2. The surgical instrument of claim 1, wherein the gripping upper and lower portions each comprise a ridged surface.

3. The surgical instrument of claim 1, wherein the angled surface of the upper jaw includes an upper gripping surface registered to loosely enmesh with a lower gripping surface on the step surface of the lower jaw.

4. The surgical instrument of claim 3, wherein the upper and lower gripping surfaces comprise a laterally ridged surface.

5. The surgical instrument of claim 1, wherein the handle portion further comprises a firing trigger operatively configured to sever tissue clamped between the upper and lower jaws and to dispense staples from the lower jaw for forming against the staple forming surface of the upper jaw.

6. A surgical instrument, comprising:
an elongate shaft defining a longitudinal axis;
a lower jaw extending distally from the elongate shaft and operatively configured to upwardly dispense staples through a staple ejecting surface thereon and further configured to be substantially flat in the longitudinal direction along the staple ejecting surface, the lower jaw further comprising a step recessed into the lower jaw distal to the staple ejecting surface, the step having a flat step surface extending distally and parallel to the longitudinal axis, the flat step surface being oriented with the staple ejecting surface and stepped downwardly therefrom;
an upper jaw pivotally attached to the lower jaw and having a staple forming surface thereon, the staple forming surface configured to be substantially flat in the longitudinal direction and containing staple pockets recessed therein, the staple forming surface positionable proximate to the staple ejecting surface of the lower jaw;
a handle portion operatively coupled to the upper jaw through the elongate shaft;
a trigger attached for movement to the handle portion and operatively configured to close the upper jaw;
an upper nonplanar gripping surface downwardly disposed on an angled surface of the upper jaw, the upper nonplanar gripping surface oriented towards the step surface of the lower jaw and spaced distal to the staple forming surface; and
a lower nonpianar gripping surface upwardly extending from the flat step surface of the lower jaw and registered to the upper gripping surface, the lower nonplanar gripping surface extending above the flat step surface and recessed below and spaced distally away from the staple ejecting surface;
wherein when said trigger is actuated to close the upper jaw proximate to the lower jaw, the upper nonplanar gripping surface and the lower nonplanar gripping surface intermesh below the staple ejecting surface.

7. The surgical instrument of claim 6, wherein the upper and lower gripping surfaces each comprise lateral ridged surfaces.

8. The surgical instrument of claim 6, wherein the handle portion further comprises a firing trigger operatively configured to actuate the firing member to sever tissue clamped between the upper and lower jaws and to dispense staples from the lower jaw for forming against the staple forming surface of the upper jaw.

9. A surgical instrument, comprising:
an elongate staple channel defining a longitudinal axis;
a stepped staple cartridge removably engaged in a distal end of the elongate staple channel to form a lower jaw, the staple cartridge comprising:
  i) a staple ejecting surface thereon extending distally in the longitudinal direction, and containing staples recessed therebelow, and
  ii) a step recessed into the stepped staple cartridge distal to the staple ejecting surface, the step having a flat step surface parallel to the longitudinal axis and at least a portion of the staple ejecting surface and stepped downwardly therefrom;
an anvil pivotally attached to the lower jaw, the anvil comprising a staple forming surface thereon which is substantially flat in the longitudinal direction and contains staple pockets recessed therein;
an elongate shaft proximally attached to the lower jaw;
a handle portion proximally attached to the elongate shaft and operatively coupled to the anvil through the elongate shaft;
a closure trigger attached for movement to the handle portion and operatively configured to close the anvil;
a firing trigger attached for movement to the handle portion and operatively configured to effect stapling by the staple cartridge and severing of tissue between the jaws;
an upper nonplanar gripping surface downwardly disposed on an angled surface of the upper jaw, the angled surface extending distally from the staple forming surface and with the upper nonplanar gripping surface spaced distally away from the staple forming surface, the upper nonplanar gripping surface oriented towards the flat step surface of the lower jaw; and
a lower nonpianar gripping surface upwardly disposed on the flat step surface of the removable stepped cartridge and registered to the upper nonplanar gripping surface for enmeshment therewith when the anvil is closed;
wherein when said trigger is actuated to close the upper jaw proximate to the lower jaw, the upper nonplanar gripping surface and the lower nonplanar gripping surface intermesh below the staple ejecting surface.

10. The surgical instrument of claim 9, wherein each of the nonplanar gripping surfaces comprises a ridged surface.

* * * * *